United States Patent [19]

Brake et al.

[11] Patent Number: 5,077,204
[45] Date of Patent: Dec. 31, 1991

[54] YEAST ENDOPEPTIDASE FOR BASIC AMINO-ACID SITE CLEAVAGE, PREPARATION AND USE

[75] Inventors: Anthony J. Brake, Berkeley; Lindley C. Blair, Los Angeles, both of Calif.; David Julius, New York, N.Y.; Jeremy W. Thorner, Berkeley, Calif.

[73] Assignees: Chiron Corporation, Emeryville; The Regents of the University of California, Berkeley, both of Calif.

[21] Appl. No.: 183,252

[22] Filed: Apr. 8, 1988

Related U.S. Application Data

[63] Continuation of Ser. No. 623,308, Jun. 21, 1984, abandoned.

[51] Int. Cl.[5] .................... C12N 9/60; C12N 15/00; C12N 1/16; C12P 21/02
[52] U.S. Cl. .................................. 435/68.1; 435/69.1; 435/71.1; 435/172.1; 435/172.3; 435/240.2; 435/252.3; 435/254; 435/255; 435/320.1; 435/224; 536/27
[58] Field of Search ................ 435/69.9, 172.3, 252.3, 435/255, 224; 586/27; 935/14, 28, 37, 48

[56] References Cited

PUBLICATIONS

Julius et al., Cell 32:839–852, 1983 (Mar.).
Wickner et al., (1976) Genetics 82:429–442.
Leibowitz et al., (1976) Proc. Natl. Acad. Sci. U.S.A., 73:2061–2065.
Bostian et al., (1983) Cell 32:169–180.
Bussey et al., (1983) Molec. Cellul. Biol. 3:1362–1370.
Skipper et al., (1984) Embo J. 3:107–111.
Julius et al., (1984) Cell 36:309–318.
Mortimer et al., in *Molecular Biology of the Yeast Saccharomyces: Metabolism and Gene Expression* (Strathern, J. N., and Broach, J. R., Eds.) pp. 639–650 (1982).
Achstetter et al., (1981) Arch. Biochem. Biophys. 207:445–454.

Primary Examiner—Richard A. Schwartz
Assistant Examiner—Richard M. Lebovitz
Attorney, Agent, or Firm—Irell & Manella

[57] ABSTRACT

Methods and compositions are provided for endopeptidase production, enhanced efficiencies of processing in vivo and in vitro to provide for process polypeptides, and purified enzyme for in vitro processing of polypeptides. The endopeptidase is specific for dibasic amino acid sites, cleaving at the C-side of the dipeptide.

The *S. cerevisiae* strain pYBCA-5 (truncated KEX2) was deposited at the A.T.C.C. on June 21, 1984 and given Accession No. 20717.

13 Claims, 8 Drawing Sheets

```
              ↓
    ValProLeuAspLysArgPheValAsnGlnHisLeuCysGlySerHisLeuValGlu
      5'-CCTTGGATAAAAGATTCGTTAACCAACACTTGTGTGGTTCTCACTTGGTTGAA
      3'-CATGGGAACCTATTTTCTAAGCAATTGGTTGTGAACACACCAAGAGTGAACCAACTT
         ^^            ^                                    ^^
    3 KPN1, 4 RSAI, 20 HINF1, 25 HIND11 HPA1, 59 HIND111, 60 ALU
    1,

AlaLeuTyrLeuValCysGlyGluArgGlyPhePheTyrThrProLysThr ArgArg Glu
    GCTTTGTACTTGGTTTGTGGTGAAAGAGGTTTCTTCTACACTCCAAAGACT AGAAGA GAA
    CGAAACATGAACCAAACACCACTTTCTCCAAAGAAGATGTGAGGTTTCTGA TCTTCT CTT
         ^         ^      ^        ^                    ^          ^
    66 RSAI, 79 HPH, 86 MNL1, 92 MB011, 113 MB011, 120 ALU1,

AlaGluAspLeuGlnValGlyGlnValGluLeuGlyGlyGlyProGlyAlaGlySerLeu
    GCTGAAGACTTGCAAGTTGGTCAAGTTGAATTGGGTGGTGGTCCAGGTGCTGGTTCTTTG
    CGACTTCTGAACGTTCAACCAGTTCAACTTAACCCACCACCAGGTCCACGACCAAGAAAC
       ^                                    ^   ^
    124 MB011, 160 ASU1 AVA2, 163 APY1 ECOR11 SCRF1,

GlnProLeuAlaLeuGluGlySerLeuGlnLysArgGlyIleValGluGlnCysCysThr
    CAACCATTGGCTTTGGAAGGTTCTTTGCAAAAGAGAGGTATTGTTGAACAATGTTGTACT
    GTTGGTAACCGAAACCTTCCAAGAAACGTTTTCTCTCCATAACAACTTGTTACAACATGA
                                                            ^
    215 MNL1, 236 RSAI,

SerIleCysSerLeuTyrGlnLeuGluAsnTyrCysAsnOC AM
    TCTATTTGTTCTTTGTACCAATTGGAAAACTACTGTAACTAATAGCGTCG-3'
    AGATAAACAAGAAACATGGTTAACCTTTTGATGACATTGATTATCGCAGCAGCT-5'
                     ^                     ^        ^^
    255 RSAI, 285 HGA1, 290 ACC1 HIND11 SAL1, 291 TAQ1,
```

FIG. I

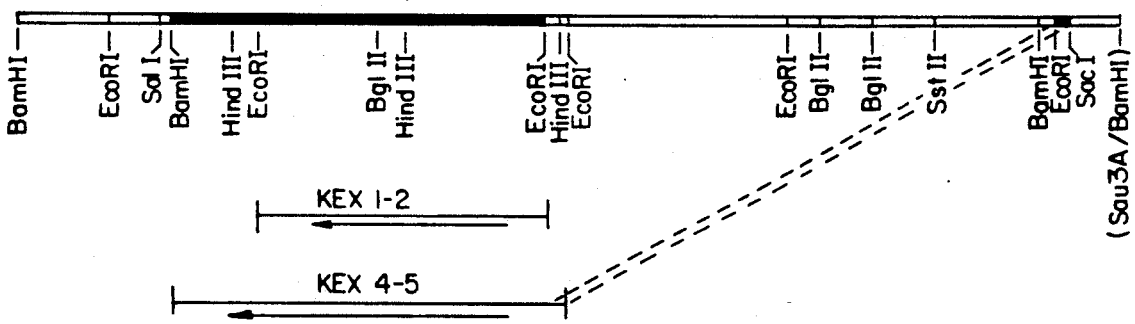
FIG. 3
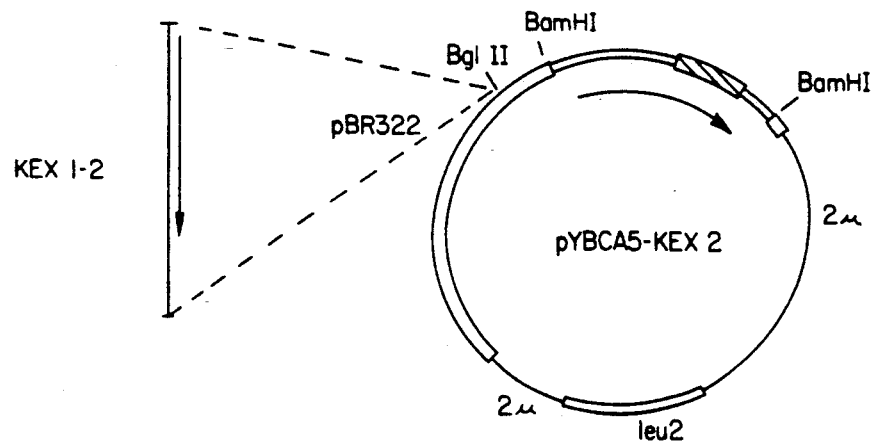
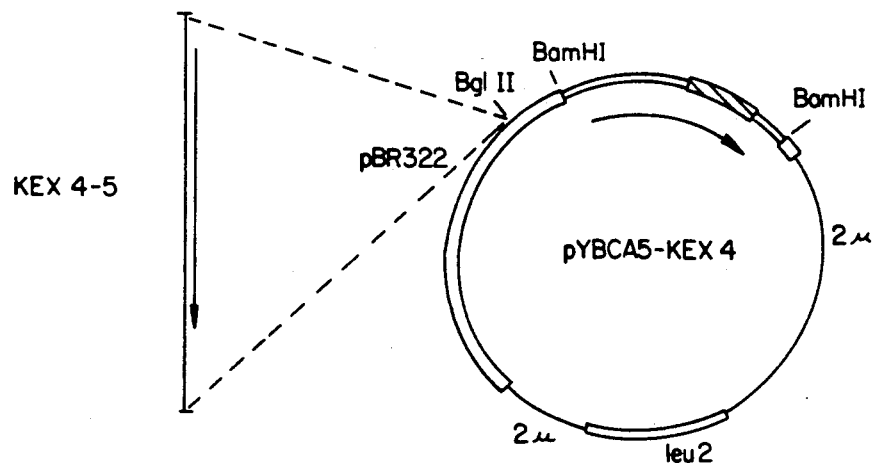
FIG. 4

GAATTCTCTGTTGACTACTAAACTGAGAGAATTTGCCGAGACTCTAAGAACAGCTTTGA
↑EcoRI

AAGAGCGTTCTGCCGATGATTCCATAATTGTCACTCTGAGAGAGCAAATGCAAAGAGAA

ACTTCAGGTTGATGTCGTTGTTCATGGACATACCTCCAGTGCAACCAAACGAGATCAAT

TCACTTGGGAATACGTTGACAAAGACAAGAAAATCCACACTATCAAATCGACTCCGTTA

GAATTTGCCTCCAAATACGCAAAATTGGACCCTTCCAGCCAGTCTCCATATGGTAAATT

AATTAAGATCGATCGTTTAGGAAACGTCCTTGGCGGAGATGCCGTGATTTACTTAAATG

TTGACAATGAAACACTATCTAAATTGGTTGTTAAGAGATTACAAAATAACAAAGCTGTC

TTTTTTGGATCTCACACTCCAAAGTTCATGGACAAGAAAACTGGTGTCATGGATATTGA

ATTGTGGACTATCCTGCCATCCTGGATAATTTACCTCACGAAAAGGCATCCGGTATTAG

ATACCATGAAAGTTTGATGACTCATGCTATGTTGATCACTGGCTGCCACGTCGATGAAA

CGTCTAAATTACCACTTCGCTACCGTCTGAAAATTCCTGGGGTAAAGACTCCGGTAAAG

ACGGATTATACGTGATGACTCAAAAGCTACTTCGAGGAGTACTGCTTTCAAATTGTGGT

CGATATCAATGAATTGCCAAAAGAGCTGGCTTCAAAATTCACCTCAGGTAAGGAAGAGC

CGATTTGTCTTGCCCATCTGGACCCAATGGTGCTTTGGCCAAATAAATAGTTTCAGCAG

CTCTGATGTAGATACACGTATCTCGACATGTTTTATTTTTACTATACATACATAAAAGA

AATAAAAAATGATAACGTGTATATTATTATTCATATAATCAATGAGGGTCATTTTCTGA

AACGCAAAAAACGGTAAATGGAAAAAAAATAAAGATAGAAAAAGAAAACAAACAAAGGA

AAGGTTAGCATATTAAATAACTGAGCTGATACTTCAAACGCATCGCTGAAGAGAACAGT

ATTGAAACCGAAACATTTTCTAAAGGCAAACAAGGTACTCCATATTGCTGGACGTGTTC

TTTCTCTCGTTTCATATGCATAATTCTGTCATAAGCCTGTTCTTTTTCCTGGCTTAAAC

ATCCCGTTTTGTAAAAGAGAAATCTATTCCACATATTTCATTCATTCGGCTACCATACT

AAGGATAAACTAAATCCCGTGTTTTTTGGCCTCGTCACATAATTATAAACTACTAACCC

```
                1                              10
             Met Lys Val Arg Lys Tyr Ile Thr Leu Cys Phe Trp
ATTATCAG     ATG AAA GTG AGG AAA TAT ATT ACT TTA TGC TTT TGG

20
Trp Ala Phe Ser Thr Ser Ala Leu Val Ser Ser Gln Gln Ile Pro
TGG GCC TTT TCA ACA TCC GCT CTT GTA TCA TCA CAA CAA ATT CCA 30                                         40
Leu Lys Asp His Thr Ser Arg Gln Tyr Phe Ala Val Glu Ser Asn
TTG AAG GAC CAT ACG TCA CGA CAG TAT TTT GCT GTA GAA AGC AAT
```

FIG.5-I

```
                                      50
    Glu Thr Leu Ser Arg Leu Glu Glu Met His Pro Asn Trp Lys Tyr
    GAA ACA TTA TCC CGC TTG GAG GAA ATG CAT CCA AAT TGG AAA TAT
                 60                                   70
    Glu His Asp Val Arg Gly Leu Pro Asn His Tyr Val Phe Ser Lys
    GAA CAT GAT GTT CGA GGG CTA CCA AAC CAT TAT GTT TTT TCA AAA
                              80
    Glu Leu Leu Lys Leu Gly Lys Arg Ser Ser Leu Glu Glu Leu Gln
    GAG TTG CTA AAA TTG GGC AAA AGA TCA TCA TTA GAA GAG TTA CAG
             90                                  100
    Gly Asp Asn Asn Asp His Ile Leu Ser Val His Asp Leu Phe Pro
    GGG GAT AAC AAC GAC CAC ATA TTA TCT GTC CAT GAT TTA TTC CCG
                                 110
    Arg Asn Asp Leu Phe Lys Arg Leu Pro Val Pro Ala Pro Pro Met
    CGT AAC GAC CTA TTT AAG AGA CTA CCG GTG CCT GCT CCA CCA ATG
                 120                                  130
    Asp Ser Ser Leu Leu Pro Val Lys Glu Ala Glu Asp Lys Leu Ser
    GAC TCA AGC TTG TTA CCG GTA AAA GAA GCT GAG GAT AAA CTC AGC
                 HindIII
                                      140
    Ile Asn Asp Pro Leu Phe Glu Arg Gln Trp His Leu Val Asn Pro
    ATA AAT GAT CCG CTT TTT GAG AGG CAG TGG CAC TTG GTC AAT CCA
             150                                  160
    Ser Phe Pro Gly Ser Asp Ile Asn Val Leu Asp Leu Trp Tyr Asn
    AGT TTT CCT GGC AGT GAT ATA AAT GTT CTT GAT CTG TGG TAC AAT
                                 170
    Asn Ile Thr Gly Ala Gly Val Val Ala Ala Ile Val Asp Asp Gly
    AAT ATT ACA GGC GCA GGG GTC GTG GCT GCC ATT GTT GAT GAT GGC
                 180                                  190
    Leu Asp Tyr Glu Asn Glu Asp Leu Lys Asp Asn Phe Cys Ala Glu
    CTT GAC TAC GAA AAT GAA GAC TTG AAG GAT AAT TTT TGC GCT GAA
                             200
    Gly Ser Trp Asp Phe Asn Asp Asn Thr Asn Leu Pro Lys Pro Arg
    GGT TCT TGG GAT TTC AAC GAC AAT ACC AAT TTA CCT AAA CCA AGA
             210                                  220
    Leu Ser Asp Asp Tyr His Gly Thr Arg Cys Ala Gly Glu Ile Ala
    TTA TCT GAT GAC TAC CAT GGT ACG AGA TGT GCA GGT GAA ATA GCT
                                 230
    Ala Lys Lys Gly Asn Asn Phe Cys Gly Val Gly Val Gly Tyr Asn
    GCC AAA AAA GGT AAC AAT TTT TGC GGT GTC GGG GTA GGT TAC AAC
                 240                                  250
    Ala Lys Ile Ser Gly Ile Arg Ile Leu Ser Gly Asp Ile Thr Thr
    GCT AAA ATC TCA GGC ATA AGA ATC TTA TCC GGT GAT ATC ACT ACG
```

FIG.5-2

```
                                          260
Glu Asp Glu Ala Ala Ser Leu Ile Tyr Gly Leu Asp Val Asn Asp
GAA GAT GAA GCT GCG TCC TTG ATT TAT GGT CTA GAC GTA AAC GAT 270                                      280
Ile Tyr Ser Cys Ser Trp Gly Pro Ala Asp Asp Gly Arg His Leu
ATA TAT TCA TGC TCA TGG GGT CCC GCT GAT GAC GGA AGA CAT TTA

290
Gln Gly Pro Ser Asp Leu Val Lys Lys Ala Leu Val Lys Gly Val
CAA GGC CCT AGT GAC CTG GTG AAA AAG GCT TTA GTA AAA GGT GTT 300                                      310
Thr Glu Gly Arg Asp Ser Lys Gly Ala Ile Tyr Val Phe Ala Ser
ACT GAG GGA AGA GAT TCC AAA GGA GCG ATT TAC GTT TTT GCC AGT

320
Gly Asn Val Val Ile Ile Arg Asn Tyr Asp Gly Tyr Thr Asn Ser
GGA AAT GTG GTG ATA ATT CGG AAT TAC GAC GGC TAT ACT AAT TCC 330                                      340
Ile Tyr Ser Ile Thr Ile Gly Ala Ile Asp His Lys Asp Leu His
ATA TAT TCT ATT ACT ATT GGG GCT ATT GAT CAC AAA GAT CTA CAT
                                              BglII

350
Pro Pro Tyr Ser Glu Val Val Pro Pro Ser Trp Gln Ser Arg Ile
CCT CCT TAT TCC GAA GTT GTT CCG CCG TCA TGG CAG TCA CGT ATT 360                                      370
Leu Gln Val Gln Ala Asn Ile Phe Ile Arg Val Val Ser Thr Ala
CTT CAG GTT CAG GCG AAT ATA TTC ATT CGA GTA GTA TCA ACG GCA

380
Asp Arg Val Ile Ala Thr Val Glu Arg Leu Arg Leu Thr Pro Leu
GAT CGA GTA ATA GCC ACG GTG GAA CGT CTG CGG CTG ACT CCA TTA 390                                      400
Ala Ala Gly Val Tyr Thr Leu Leu Leu Glu Ala Asn Pro Asn Leu
GCT GCC GGT GTT TAC ACT TTG TTA CTA GAA GCC AAC CCA AAC CTA

410
Thr Trp Arg Asp Val Gln Tyr Leu Ser Ile Leu Ser Ala Val Gly
ACT TGG AGA GAC GTA CAG TAT TTA TCA ATC TTG TCT GCG GTA GGG 420                                      430
Leu Glu Lys Asn Ala Asp Gly Asp Trp Arg Asp Ser Ala Met Gly
TTA GAA AAG AAC GCT GAC GGA GAT TGG AGA GAT AGC GCC ATG GGA

440
Thr Lys Tyr Ser His Arg Tyr Gly Phe Gly Lys Ile Asp Ala His
ACG AAA TAC TCT CAT CGC TAT GGC TTT GGT AAA ATC GAT GCC CAT 450                                      460
Lys Leu Ile Glu Met Ser Lys Thr Trp Glu Asn Val Asn Ala Gln
AAG TTA ATT GAA ATG TCC AAG ACC TGG GAG AAT GTT AAC GCA CAA
```

FIG. 5-3

```
                                    470
        Thr Trp Phe Tyr Leu Pro Thr Leu Tyr Val Ser Gln Ser Thr Asn
        ACC TGG TTT TAC CTG CCA ACA TTG TAT GTT TCC CAG TCC ACA AAC 480                                     490
        Ser Thr Glu Glu Thr Leu Glu Leu Arg His Asn His Ile Arg Lys
        TCC ACG GAA GAG ACA TTA GAA CTC CGT CAT AAC CAT ATC AGA AAA

500
        Ser Leu Gln Asp Ala Asn Phe Lys Arg Ile Glu His Val Thr Val
        AGT CTT CAA GAT GCT AAC TTC AAG AGA ATT GAG CAC GTC ACG GTA 510                                     520
        Thr Val Asp Ile Asp Thr Glu Ile Arg Gly Thr Thr Leu Ser Asp
        ACT GTA GAT ATT GAT ACA GAA ATT AGG GGA ACT ACA CTG TCT GAT

530
        Leu Ile Ser Pro Ala Gly Ile Ile Ser Asn Leu Gly Val Val Arg
        TTA ATA TCA CCA GCG GGG ATA ATT TCA AAC CTT GGC GTT GTA AGA 540                                     550
        Pro Arg Asp Val Ser Ser Glu Gly Phe Lys Asp Trp Thr Phe Met
        CCA AGA GAT GTT TCA TCA GAG GGA TTC AAA GAC TGG ACA TTC ATG

560
        Ser Val Ala His Trp Gly Glu Asn Gly Val Gly Asp Trp Lys Ile
        TCT GTA GCA CAT TGG GGT GAG AAC GGC GTA GGT GAT TGG AAA ATC 570                                     580
        Lys Val Lys Thr Thr Glu Asn Gly His Arg Ile Asp Phe His Ser
        AAG GTT AAG ACA ACA GAA AAT GGA CAC AGG ATT GAC TTC CAC AGT

590
        Trp Arg Leu Lys Leu Phe Gly Glu Ser Ile Asp Ser Ser Lys Thr
        TGG AGG CTG AAG CTC TTT GGG GAA TCC ATT GAT TCA TCT AAA ACA 600                                     610
        Glu Thr Phe Val Phe Gly Asn Asp Lys Glu Glu Val Glu Pro Ala
        GAA ACT TTC GTC TTT GGA AAC GAT AAA GAG GAG GTT GAA CCA GCT

620
        Ala Thr Glu Ser Thr Val Ser Gln Tyr Ser Ala Ser Ser Thr Ser
        GCT ACA GAA AGT ACC GTA TCA CAA TAT TCT GCC AGT TCA ACT TCT 630                                     640
        Ile Ser Ile Ser Ala Thr Ser Thr Ser Ser Ile Ser Ile Gly Val
        ATT TCC ATC AGC GCT ACT TCT ACA TCT TCT ATC TCA ATT GGT GTG

650
        Glu Thr Ser Ala Ile Pro Gln Thr Thr Thr Ala Ser Thr Asp Pro
        GAA ACG TCG GCC ATT CCC CAA ACG ACT ACT GCG AGT ACC GAT CCT 660                                     670
        Asp Ser Asp Pro Asn Thr Pro Lys Lys Leu Ser Ser Pro Arg Gln
        GAT TCT GAT CCA AAC ACT CCT AAA AAA CTT TCC TCT CCT AGG CAA
```

FIG.5-4

```
                                        680
Ala Met His Tyr Phe Leu Thr Ile Phe Leu Ile Gly Ala Thr Phe
GCC ATG CAT TAT TTT TTA ACA ATA TTT TTG ATT GGC GCC ACA TTT 690                                         700
Leu Val Leu Tyr Phe Met Phe Met Lys Ser Arg Arg Arg Ile
TTG GTG TTA TAC TTC ATG TTT TTT ATG AAA TCA AGG AGA AGG ATC

710
Arg Arg Ser Arg Ala Glu Thr Tyr Glu Phe
AGA AGG TCA AGA GCG GAA ACG TAT GAA TTC
                                    ↑EcoR1

Translated Mol. Weight = 79917.74
```

FIG. 5-5

200
YEAST ENDOPEPTIDASE FOR BASIC AMINO-ACID SITE CLEAVAGE, PREPARATION AND USE

This invention was made with U.S. Government support under Grant No. GM-21841 awarded by the Department of Health and Human Services. The U.S. Government may have certain rights in this invention.

This application is a continuation of application Ser. No. 623,308, filed June 21, 1984, now abandoned.

BACKGROUND OF THE INVENTION

1. Field of the Invention

A significant number of cellular functions are predicated on the ability to secrete certain polypeptides. The signal for secretion appears to be a leader sequence which is predominantly hydrophobic in nature joined to the mature peptide through a processing oligopeptide signal recognized by an endopeptidase. The ability to secrete polypeptides foreign to a host is very attractive, since there may be substantially less degradation of the desired product and where the natural product has an amino acid other than methionine as the first amino acid, the secreted product will have the correct N-terminus. Where secretion is obtained at high efficiency a more efficient and economic production of the desired polypeptide may result.

Secretion of the desired polypeptide has many attractions. As indicated, the probability of degradation of the polypeptide is diminished, where the intracellular lifetime of the polypeptide is short. Furthermore, where the polypeptide is retained intracellularly, it is necessary to isolate and lyse the cells, and separate the polypeptide of interest from the total cellular protein. By contrast, where the polypeptide is secreted, one can continuously withdraw the nutrient medium, isolating the protein of interest where the protein background is substantially smaller. Furthermore, in many cases the enhanced concentration of the polypeptide in the host can be lethal to the host or substantially diminish the viability of the host. In these cases, the production of the deslies polypeptide will be relatively small. Where a fused polypeptide is employed, having a signal leader sequence, the signal leader may not only serve to provide for secretion, but also mask the lethal character of the foreign polypeptide.

There are a substantial number of different endopeptidases present in cells. These endopeptidases have different specificities, so as to require different sequences and/or conformations of the polypeptide as the cleavage site. With hybrid DNA technology, one tries to provide a high level of production of a polypeptide product, which is in addition to the normal cellular products. Where such polypeptide requires processing, the cell may not be able to respond to the increased processing load. However, the mere fact of providing for enhanced genetic capability of producing the endopeptidase is no assurance that there will be an enhanced or more efficient processing of the endopeptidase substrate.

2. Description of the Prior Art

S. cerevisiae mutants having a lesion associated with killer toxin expression and α-factor pheromone expression are described by Wickner and Leibowitz, *Genetics* (1976) 82:429–442; Leibowitz and Wickner, *Proc. Natl. Acad. Sci. USA* (1976) 73:2061–2065. The required processing of killer toxin and α-factor precursors is described by Bostian et al., *Cell* (1983) 32:169–180; Bussey et al., *Molec. Cellul. Biol.* (1983) 3:1362–1370 and Skipper et al., *EMBO J.* (1984) 3:107–111, Julius et al., *Cell* (1983) 32:839–852 and Julius et al., *Cell* (1984) 36:309–318. Mapping of the lesion associated with loss of killer activity may be found in Wickner and Leibowitz (1976), supra; and Mortimer and Schild, (1982) "Genetic Map of *Saccharomyces cerevisiae*." In *Molecular Biology of the Yeast Saccharomyces: Metabolism and Gene Expression*, (Strathern, J. N., Jones, E. W., and Broach, J. R., Eds.) Cold Spring Harbor Laboratory, NY, pp. 639-350. Proteinase M reported by Achstetter et al., *Arch. Biochem. Biophys.* (1981) 207:445–454, appears to have activities analogous to the product of the KEX2 gene.

SUMMARY OF THE INVENTION

DNA sequences are provided for expression of an endopeptidase, product of the KEX2 gene, involved with processing during secretion. The DNA sequences can be used for production of the endopeptidase in high yields for purified samples of the endopeptidase, or for enhanced intracellular production of the endopeptidase for efficient processing of naturally occurring or fused polypeptides having processing sites recognized by the KEX2 endopeptidase.

BRIEF DESCRIPTION OF THE DRAWINGS

FIG. 1 is the sequence for the fragment designated BCA-5 coding for peptide B, C and A of human proinsulin;

FIG. 3 is a restriction map of the genomic fragment containing the KEX2 gene in pJ2B;

FIG. 4 is a pictorial of the plasmids pYBCA5-KEX2 and pYBCA5-KEX4; and

FIG. 5 is a partial DNA sequence of the KEX2 gene and predicted amino acid sequence.

DESCRIPTION OF THE SPECIFIC EMBODIMENTS

Figure 2:
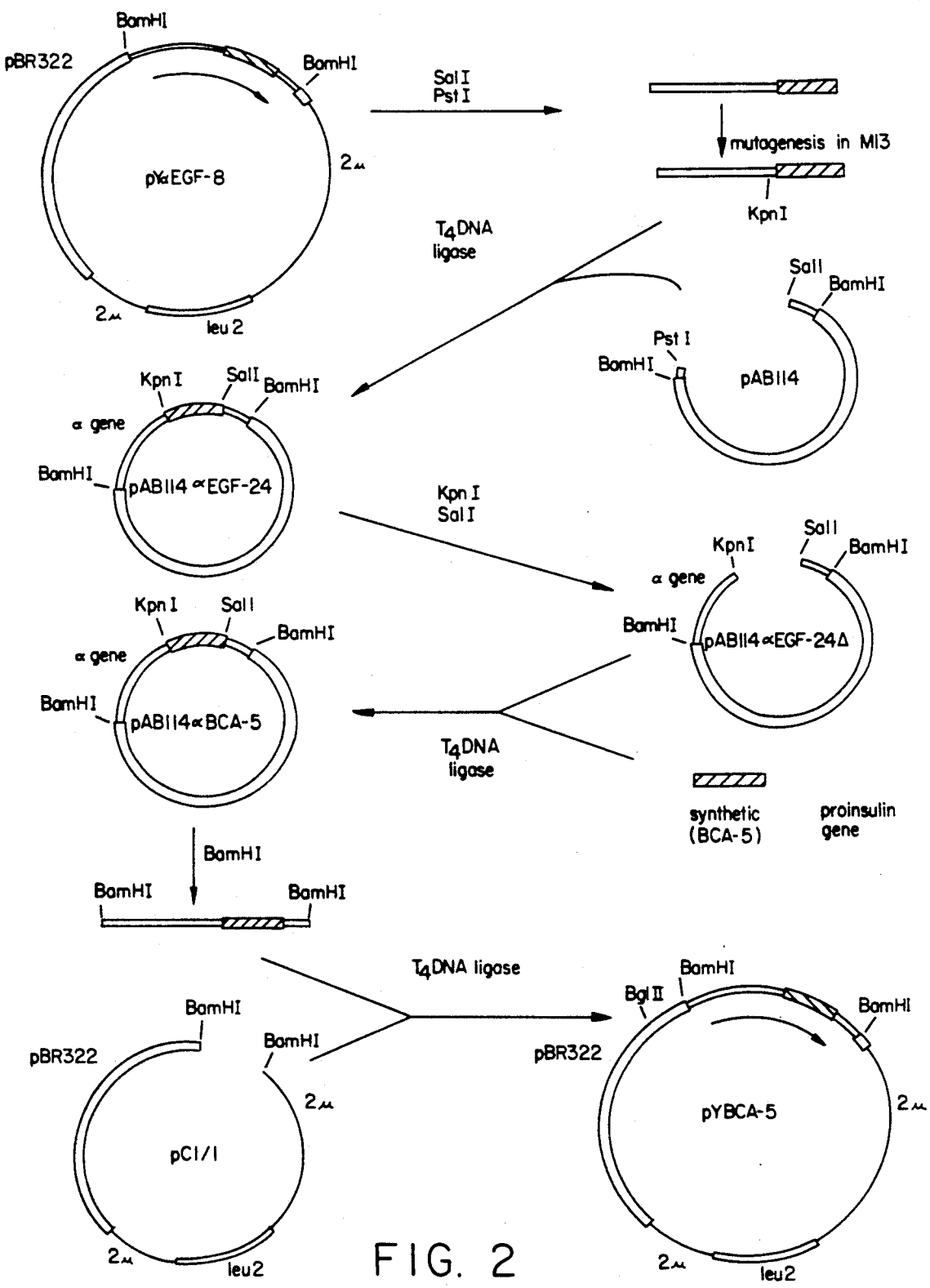
FIG. 2 is a flow chart of the preparation of pYBCA-5.

DNA sequences, constructs containing the DNA sequences, and hosts containing the constructs are provided for use in processes for production of an endopeptidase, product of an endopeptidase gene, and for efficient secretion of natural and unnatural expression products in a unicellular microorganism host. (By "unnatural" is intended a DNA sequence different from the DNA sequence normally associated with the leader sequence and processing signal, as well as the amino acid sequence coded by these DNA sequences. By "foreign" is intended a DNA sequence which is not naturally present in the host.) The KEX2 gene is a single copy gene.

In one aspect of the subject invention, enhanced processing of a precursor polypeptide to a mature polypeptide is achieved by introducing into a yeast host cell DNA sequences coding for an endopeptidase and for the precursor polypeptide. The precursor polypeptide and endopeptidase are related in that the precursor has at least one selectively cleavable peptide bond, which is cleavable by the endopeptidase. The transcriptional initiation of the endopeptidase allows for an enhanced production and percent of total protein of the endopeptidase as compared to the unmodified host, where either constitutive or inducible transcription occurs.

A DNA sequence is provided encoding for an endopeptidase from a unicellular microorganism, particularly fungal, more particularly yeast, specifically Saccharomyces, Schizosaccharomyces, or Kluveromyces, more specifically *S. cerevisiae, S. carlsbergensis, S. pombe,* or *K. lactis.* The enzyme is characterized by cleaving on the carboxyl side of an internal dipeptide of basic amino acids, particularly arginine and lysine, more particularly having arginine at the C-terminus. The endopeptidase is effective in the processing of yeast-α-factor and killer toxin, so that the wild-type host having a functional KEX2 gene is detectable by the production of the α-pheromone; by mating with the a-type yeast, and in those yeast hosts capable of expressing the precursor to killer toxin, by secretion of mature killer toxin.

The DNA sequence may be obtained as a restriction fragment of less than 10 kbp, preferably up to and including about 5 kb. In yeast, the KEX2 gene is further characterized by being present on an about 4.5 kb EcoRI-BamHI fragment, which fragment has a unique BglII restriction site.

The 4.5 kb EcoRI-BamHI fragment not only includes the KEX2 gene, but also the necessary transcriptional and translational regulatory signals for expression in yeast, as well as other organisms, for example, prokaryotes, e.g., *E. coli.* The natural transcriptional and translational regulatory signals need not be used with the KEX2 gene, since the KEX2 gene can be severed from the naturally occurring regulatory signals and joined to other transcriptional and translational regulatory signals. However, to the extent that the termination region is recognized by the host in which the KEX2 gene is to be expressed, conveniently the termination region may be retained.

The KEX2 transcriptional regulatory region may be modified in a number of ways, by substitution, by addition of one or more promoters to provide for tandem promoters, by introduction of regulatory regions, which allow for inducible expression as a result of a change in the physical or chemical environment, e.g., the presence or absence of metabolites, a change in the carbon source, a change in temperature, e.g., from a non-permissive to a permissive temperature, a change in nutrient concentration, e.g., phosphate, or the like. Thus, the sequence upstream from the transcriptional initiation site may be changed to introduce the various sequences which allow for constitutive or inducible expression, that is, from non-permissive to permissive conditions.

Depending upon the particular host, various transcriptional regulatory regions may be employed, such as the transcriptional regulatory regions of the yeast glycolytic enzymes, such as alcohol dehydrogenase, glyceraldehyde-3-phosphate dehydrogenase, phosphoglucoisomerase, pyruvate kinase, phosphofructokinase, glucose-6-phosphate dehydrogenase, etc. or other strong transcriptional regulatory region, e.g., acid phosphatase.

The transcriptional and/or translational initiation sites may be determined by various techniques. The 4.5 kb EcoRI-BamHI fragment may be restriction mapped and partially or completely digested with different restriction enzymes to yield fragments which may then be isolated, cloned and sequenced, so as to determine the sequence of the EcoRI-BamHI fragment. Various smaller fragments may be examined to determine whether expression of the KEX2 gene is still obtained, so that the restriction site may be established as being present at a site removed from the regulatory domains and structural gene. Alternatively, the EcoRI-BamHI fragment may be joined to DNA sequences at either end and resected with Bal31 for varying times, so as to determine the approximate extent of DNA which must be removed to destroy transcriptional capability. For those sequences incapable of independent transcription when introduced into a host, the sequence can be introduced into an expression vector to determine whether the structural gene is present and sufficiently intact to code for an active endopeptidase. It may be sufficient or desirable to remove or add one or more amino acids from at the N-or the C-terminus, while still retaining the endopeptidase activity.

In addition to the manipulation of the flanking regions, removing all or portions of the flanking regions, usually providing for less than about a 2kb flanking region, more usually less than about a 1 kb flanking region, the structural gene may also be manipulated by varying individual nucleotides, while retaining the correct amino acid(s) or varying the nucleotides, so as to modify the amino acids, without loss of enzymatic activity. Nucleotides may be substituted, inserted or deleted by such techniques as in vitro mutagenesis and primer repair. The structural gene may be truncated at the 3'-terminus while retaining its endopeptidase activity removing not more than about 60 codons, usually not more than about 45 codons or adding not more than 60, usually not more than about 45 codons to the whole or truncated gene.

After the KEX2 structural gene has been manipulated to the desired size, depending upon the changes in the flanking regions, various constructs can now be prepared. Where the transcriptional and translational initiation and termination regions have been retained, and these regions are functional in the projected host, the KEX2 structural gene with its flanking regions may be inserted into an appropriate replication vector.

The replication vector is characterized by having an efficient replication system, having a high or low copy number where "low" intends from about 1 to 5 copies, and "high" intends greater than 5, usually not exceeding about 100, more usually not exceeding about 50. The replication system will be capable of replication in a unicellular microorganism host and may be capable of replication in more than one unicellular microorganism host. Hosts of particular interest include prokaryotes and eukaryotes, such as *E. coli, B. subtilis, S. cerevisiae,* or the like. Frequently, it is desirable to have replication systems recognized by more than one organism, particularly two organisms, such as *E. coli* and yeast. These vectors will be referred to as shuttle vectors, since they will replicate in more than one host.

The replication systems may be derived from plasmids, both cytoplasmic and mitochondrial, viruses, chromosomes, where a centromere and one or more sequences encoding for autonomously replicating segments are employed, or the like. Where integration is desired, one can achieve integration in a variety of ways, with or without replication systems recognized by the intended host, employing autonomously replicating segments, transposons, Ti or Ri sequences, or DNA sequences homologous to the host genome.

While it will not be necessary to have a structural gene present on the vector which allows for selection, referred to as markers, so that there may be none of such structural genes, for the most part, there will be from 1 to 3 markers, more usually from 1 to 2 markers, which provide for selection of host cells containing the vector. The vectors may be associated with providing prototrophy to an auxotrophic host, such as his⁻, leu⁻, trp⁻, ura⁻, or the like; resistance to a biocide or biostat, such as kan$^r$, str$^r$, tun$^r$, amp$^r$, cam$^r$, tet$^r$, etc. or to heavy metals, such as copper and mercury or to toxins, such as colicin; immunity; etc. Desirably, where there are a plurality of markers, one of the markers will have a unique restriction site, where insertion of a cassette (to be described below) or the KEX2 gene with its regulatory sequences will produce loss of the marker which will be indicative of the presence of the KEX2 gene.

Where the transcriptional and translational initiation regulatory region and/or the transcriptional and translational termination regions have been removed, they may be replaced by other regions recognized by the intended host. Conveniently, cassettes can be prepared where the initiation and termination regions are separated by a "polylinker," which provides for a plurality of restriction sites, so that the KEX2 gene can be inserted or substituted into the region intermediate the initiation and termination regions, so as to be under the transcriptional and translational regulatory control of the sequences present in those regions. For expression in yeast, it may be desirable to provide transcriptional and translational regulatory regions from the yeast glycolytic enzymes described previously, where the termination region may be associated with the same or different structural gene associated with the initiation region.

Where one is solely interested in the production and isolation of the KEX2 gene expression product for use in vitro, it will be sufficient to transform an appropriate host and allow for expression of the KEX2 gene. As already indicated, regulatory signals may be employed which are inducible, so that expression can be induced at the appropriate time.

For in vitro use, host cells may be lysed and the membrane fragments isolated by conventional techniques. These fragments containing enhanced amounts of the KEX2 endopeptidase may be used as is, or fixed to a solid substrate for use in processing polypeptides. The membranes may be dispersed in an aqueous medium at about optimal pH, particle bound membrane may be packed in a column or other useful configuration may be employed. Alternatively, the KEX2 enzyme may be purified for use.

Of equal or greater interest is the use of the endopeptidase coded for by the KEX2 gene in vivo in conjunction with the expression of an unnatural or foreign polypeptide ("expression product"). The expression product will be one which precursor has a processing site recognized by the endopeptidase expressed by the KEX2 gene. This will be particularly valuable where the expression product is to be secreted and the signal or leader peptide sequence is joined to the expression product by a processing signal recognized by the KEX2 endopeptidase. In this manner, the natural level of the endopeptidase may be greatly enhanced, so as to more efficiently process the expression product precursor.

Conveniently, one may use signal leaders associated with wild-type proteins secreted by the host. For example, in yeast, one can use the signal leader sequence associated with α-factor precursor, killer toxin precursor, or possibly, SST1 precursor. Thus, the DNA sequences coding for these leader sequences would be joined through the basic dipeptide processing signal to the structural gene coding for the expression product to provide expression of the precursor of the expression product.

Where a prokaryotic host is employed, a structural gene coding for the expression product precursor could be inserted intermediate the stop codons of the KEX2 gene and the transcriptional termination region, so as to provide an operon under the transcriptional regulatory control of a single promoter region. Alternatively, the structural gene of the expression product precursor could be inserted intermediate the transcriptional initiation region and the KEX2 gene, where the structural gene for the expression product precursor has its own stop codons, provides for an untranslated region between the two genes, and each of the genes has its own Shine-Dalgarno or ribosomal binding site, so as to provide for efficient translation. It is also feasible to have a transcriptional terminator sequence intermediate the two genes, where RNA polymerase can read through such termination sequence.

Where, however, a eukaryotic host is employed, e.g., yeast, it will be necessary that each of the structural genes has its own transcriptional and translational regulatory regions. As indicated above, one can prepare cassettes having appropriate termini and having the transcriptional and translational initiation and termination regions separated by a sequence providing for one or more restriction sites, particularly a plurality of restriction sites. Thus, the cassettes can be inserted into an appropriate vector having the appropriate replication system(s) and marker(s) at appropriate restriction sites, where the two genes will be present on the same vector.

While it is not necessary that one have the same transcriptional regulatory initiation region for the two structural genes, in many instances this will be advantageous so that expression of the two genes is coordinated. Alternatively, one may wish to be able to independently induce expression, so that two different transcriptional regulatory sequences would be employed.

In some instances, it may desirable to have a plurality of copies, two or more, of the gene expressing the expression product precursor in relation to the KEX2 gene. This can be achieved in a variety of ways. For example, one may use separate plasmids, where the plasmid having the expression product precursor has a higher copy number than the plasmid containing the KEX2 gene. In this situation it would be desirable to have different markers on the two plasmids, so as to ensure the continued maintenance of the plasmids in the host. Alternatively, one could integrate one or both genes in the host genome and associate the expression product precursor gene with an amplifying gene, such as the dihydrofolate reductase gene, or one of the metallothionein genes, as described in Karin et al., *Proc. Natl. Acad. Sci. USA* (1984) 81:337–341; Schimke, *Scientific American* (1980) 243:60–69; and Wigler et al., *Proc. Natl. Acad. Sci. USA* (1980) 77:3567–3570. Thus, the expression product precursor gene could be amplified, so as to have a plurality of copies in the genome.

Alternatively, one could employ two transcriptional regulatory regions having different rates of transcriptional initiation, providing for enhanced expression of the expression product precursor gene in relation to the KEX2 gene. A wide variety of promoters are known, so that the appropriate promoters can be readily selected and employed. Finally, one can use different promoters, where one promoter provides for a low level of constitutive expression of the KEX2 gene, while the second promoter provides for a high level of induced expression of the expression product precursor.

Expression products of interest include enzymes, hormones, e.g., insulin, ACTH, etc., lymphokines, membrane surface proteins, proteins from pathogens for vaccines, structural proteins, immunoglobulins, blood proteins, or the like. The particular structural gene which is inserted is not critical to this invention and any polypeptide or protein of interest which with the leader and processing signal can serve as a substrate for the KEX2 endopeptidase may be employed.

The KEX2 gene or genes encoding for polypeptides having KEX2 endopeptidase-like activity, from yeast or other prokaryotic or eukaryotic source, can be isolated from an appropriate host in the following way. Yeast mutants which are deficient in expression of functional α-factor or functional killer toxin are available from a variety of sources or may be made so by appropriate mutation. A gene library may then be employed, either chromosomal or cDNA, particularly cDNA. Higher eukaryotic multicellular hosts may be used for complementation. Mutant host cells, e.g., yeast spheroplasts, may be transformed with the library in plasmid vectors and the transformed cells screened for their ability to process an appropriate naturally occurring protein. Those cells which prove to be positive, can be reexamined and further tested to determine whether one or more other deficiencies have been restored. For example, where the KEX2 gene is in yeast, both the α-factor and killer toxin can be used as diagnostic of KEX2 competence.

Once the plasmid(s) have been isolated, which are putatively positive for the KEX2 gene, these plasmids may be manipulated to isolate and characterize the DNA fragment carrying the putative KEX2 gene. The fragment, which will usually be in the range of 1-5 kb when a cDNA is used or usually in the range of about 5-25 kb when chromosomal DNA is used, may be restriction mapped or digested with one or more different restriction enzymes, either individually or simultaneously, and the fragments cloned and tested for complementation. In this manner, new smaller fragments are achieved which may be more readily analyzed and characterized. By subcloning and deletion mapping, the area specifying the structural gene and the flanking regions defining the regulatory signals may be identified. By sequencing, overlapping fragments can be identified, where the fragments contain only a partial sequence of the structural gene and/or regulatory domains. These fragments may then be restriction mapped, so that the fragments may be joined to provide for the complete structural gene, including to the extent desired, the flanking regions.

The manipulated DNA sequence may then be introduced into an appropriate expression vector or where the regulatory signals are retained for the KEX2 gene, introduced into an appropriate vector which need not have a cassette for the regulation of expression.

Depending upon the nature of the construction, the structural gene having the secretory leader sequence may be inserted into the same vector carrying the KEX2 gene or a different vector. The expression product structural gene may be present in the host as a result of integration, as a result of being present on the KEX2 gene carrying vector or by virtue of introduction of a separate plasmid into the host.

The modified host may then be grown in an appropriate nutrient medium, which allows for stable maintenance of the plasmid(s) present in the modified yeast host. Where the expression product gene is under inducible control, the yeast host may be grown to high density, that is a density of at least an OD of about 2 at 650 nm, and expression induced. Alternatively, where expression is constitutive, the product will be continuously expressed into the medium and the nutrient medium may be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to substantially remove any yeast proteins which are also secreted in the medium or result from lysis of yeast cells, so as to provide a product which is at least substantially free of host debris, e.g, proteins, lipids and saccharides; the debris being less than about 0.5, usually less than 0.1 weight percent, but may have detectable amounts of the host debris.

EXPERIMENTAL

Materials

Synthetic peptides were purchased from Peninsula Laboratories or Vega-Fox Biochemicals. Sources for all other reagents and enzymes used are given in Brake et al., Molec. Cellul. Biol. (1983) 3:1440–1450; J. Cellul. Biochem. (Suppl.) (1983) 7B:375; and Julius et al., Cell (1983) 32:839–852; ibid (1984) 36:309–318.

Organisms and Growth Conditions.

The yeast strains used in this study are listed in Table 1. The compositions of minimal medium (SD), rich broth medium (YPD), and selective medium (SC-Ura) for the propagation of yeast strains harboring the plasmid YEp24 and its derivatives, have been described by others (Sherman et al, 1979, *Methods in Yeast Genetics: A Laboratory Manual*, Cold Spring Harbor Laboratory, N.Y.). The low sulfate medium (LSM) used for labelling yeast cells is a minimal medium (Sherman, supra) which has chloride salts instead of sulfate salts. Plasmid pAB102 is a derivative of YEp24 carrying an insert (11.4 kb) containing the MFα1 gene and was isolated from a genomic library by the method described in Brake et al., (1983) supra. See also, copending U.S. application Ser. No. 522,909, which appropriate disclosure is incorporated herein by reference.

Radiolabeling and Immunoprecipitation of α-Factor-Related Antigens

Procedures for labeling of cells with $[^{35}S]SO_4^{-2}$ in the presence and absence of tunicamycin, preparation of cell lysates, immunoprecipitation of α-factor-related antigens from lysates and from cell-free culture fluid, electrophoresis of immunoprecipitates in polyacrylamide gels, and autoradiography, have all been described in detail previously (Julius et al, 1983, 1984, supra). Preparation of polyA+ RNA from MATα cells, translation of the mRNA in a wheat germ extract, and immunoprecipitation of the α-factor-related translation products were all conducted as described before (Brake et al., 1983, supra).

Bioassays for Pheromone Activity, Killer Toxin Secretion, and Mating Type

Agar diffusion ("halo") assays for measuring production of biologically-active α-factor were performed with a lawn of the super-sensitive indicator strain RC634 (MATa sst1-3), as described by Julius et al. 1983, supra. Similar agar diffusion assays for secretion of biologically-active killer toxin were performed with a lawn of the sensitive indicator DC17 (MATα [KIL-0]), according to the procedure of Wickner and Leibowitz 1976, supra. Mating type determinations were conducted by prototroph selection after crossing the strains to be tested to standard MATa and MATα strains (DC227 and XBH6-13D, respectively) carrying complementing auxotrophic markers (Sherman et al., 1979, supra).

Assay of Endopeptidase Activity in Permeabilized Cells and in Isolated Membrane Fractions Permeabilization of whole yeast cells with the non-ionic detergent Brij 58, preparation of crude membrane fractions, and measurement of protein concentration were conducted by the methods described previously (Julius et al., 1983, supra), incorporated herein by reference. To measure peptidase activity, samples of permeabilized cells or membrane material were added to a reaction mixture containing 0.1–0.5 mM fluorogenic peptide substrate (added from a 20 mM stock dissolved in DMSO) and 200 mM HEPES-Tris (pH 7.0), in a final volume of 0.4 ml. Following incubation for 30 min at 37° C., whole cells were removed by centrifugation in a microfuge (Eppendorf) and membrane material was removed by $Ba(OH)_2$-$ZnSO_4$ precipitation. The amount of fluorescence formed in the supernatant solution was determined in a fluorescence spectrophotometer (Perkin-Elmer, Model MPF-44B), set either at an excitation wavelength of 335 nm and an emission wavelength of 410 nm (for measurement of β-naphthylamine) or at an excitation wavelength of 380 nm and an emission wavelength of 460 nm (for measurement of 7-amino-4-methyl-coumarin, AMC). To determine the number of moles of substrate hydrolyzed, the fluorescence yield of samples was compared to a standard curve prepared with known concentrations of authentic AMC dissolved in the same buffer. The generation of AMC was linear with respect to both time (for at least 30 min) and the concentration of either permeabilized cells (up to $5 \times 10^7$ ml) or membrane protein (up to 1 mg/ml), as long as substrate conversion did not exceed 30–40%.

For analysis of the pattern of substrate cleavage, reactions were carried out on a larger scale (1.6 ml total volume) in a volatile buffer, 0.2M pyridine-acetate (pH 7.0). Samples (250 μl) were removed at various times and quenched by dilution into 30 μl glacial acetic acid. Membrane material was removed from the quenched incubation mixtures by filtration through a membrane filter (0.2μ). The filtrates were taken to dryness in a centrifugal concentrator and redissolved in 10 μl 50 % aqueous pyridine. The redissolved material was spotted onto the diatomaceous earth strip at the origin of the lanes of a scored silica gel thin layer plate (Whatman, LK5D). Ascending chromatography was performed in the solvent system of Ciejek and Thorner, Cell (1979) 18:623-635. Arginine-containing peptides were revealed under long wavelength ultraviolet light after reaction with a fluorogenic spray reagent, phenanthrenequinone, as described by McDonald and Ellis, Life Sci. (1975) 17:1269–1276. AMC was revealed by its intrinsic fluorescence. Plates were photographed with Polaroid Type 55 film using a Polaroid MP-4 camera.

Isolation of Plasmid pJ2B from a Yeast Genomic DNA Library

Spheroplasts of strain XBH16-15A (MATα kex2-1 ura3-52 leu2-3,112) were prepared and transformed (Beggs, Nature (1978) 275:104–109) separately with two different yeast genomic libraries constructed by insertion of partial Sau3A digests of chromosomal DNA into the BamHI sites of either YEp13 (Nasmyth and Reed, Proc. Natl. Acad. Sci. USA (1980) 77:2119–2123) or YEp24 (Carlson and Botstein, Cell (1982) 28:145–154). Approximately 2,700 Leu+ (YEp13) and about 3,500 Ura+ (YEp2 transformants were picked from the regeneration agars and transferred as small patches to plates containing an appropriate selective medium (either SC-Leu or SC-Ura). The patches were scored for secretion of α-factor by halo assay. DNA was prepared from the positive candidates as described in Brake et al., (1983) supra, and used to transform E. coli HB101, selecting for ampicillin-resistance (Maniatis et al., (1982) Molecular Cloning: A Laboratory Manual, Cold Spring Harbor Laboratory, NY). Plasmid DNA was prepared on a large scale from the bacterial transformants and used to re-transform the original yeast recipient and the transformants tested for production of α-factor again. Positive clones that survived the second re-test were scored for the production of killer toxin by halo bioassay and for mating competence. Only one of the initially obtained candidates (pJ2B), which was isolated from the library in YEp24, was able to reproducibly complement all three of the phenotypic manifestations characteristic of the kex2-1 mutation carried by the recipient strain.

Detergent-permeabilized kex2 cells carrying the pJ2B plasmid hydrolyzed CBZ-AlaArgArg-β-naphthylamide (not shown), Boc-GlnArgArg-7-amino-4-methyl-coumarin (MCA) and Boc-GluLysLys-MCA at rates six- to ninefold greater than kex2 cells harboring the vector alone, although both of the arginine-containing substrates were hydrolyzed nearly 30 times faster than the lysine-containing substrate. These differences were even more dramatic when membrane fractions of such transformed cells were assayed. Depending on the experiment, membranes from kex2 cells carrying the pJ2B plasmid hydrolyzed Boc-GlnArgArg-MCA at rates 20- to 35-fold greater than membranes from kex2 cells carrying YEp24 (Table 2). Boc-GluLysLys-MCA was hydrolyzed about 50 times more slowly and the increment between the pJ2B- and YEp24-containing cells was not nearly as pronounced (about six-fold). That the activity being measured was rather specific for substrates containing a pair of basic residues and showed a marked preference for arginine over lysine was supported by several additional results (Table 2). Membrane fractions from kex2 cells transformed with plasmid pJ2B showed no significant increase in their ability to attack aminopeptidase substrate (Arg-MCA or Leu-MCA). Two endopeptidase substrates containing single arginine residues (Bz-Arg-MCA and Boc-IleGluGlyArg-MCA) were hydrolyzed at negligible rates and a third such peptide (Boc-PheSerArg-MCA) was hydrolyzed about three times more slowly than Boc-GlnArgArg-MCA.

Properties of the Specific KEX2 Endopeptidase

Although kex2 cells carrying the pJ2B plasmid displayed a dramatic elevation in an enzyme specific for the hydrolysis of substrates with a pair of basic residues, these peptides were slowly attacked by activities present in control cells transformed with the vector alone. To further distinguish between the specific KEX2 endopeptidase and the background activities, a variety of inhibitors and conditions were examined. The activities present in kex2 cells transformed with YEp24 alone were sensitive to inhibition by the serine protease inhibitors phenylmethylsulfonyl fluoride (PMSF), tosyl-lysine-chloromethylketone (TLCK) and tosyl-phenylalanine-chloromethylketone (TPCK); whereas, the specific endopeptidase over-produced in kex2 cells transformed with plasmid pJ2B was completely resistant to these inhibitors (Table 3). The specific endopeptidase, but not the background activity, was quite sensitive to inhibition by $Zn^{++}$ and by other heavy metals including $Cu^{++}$ and $Cd^{++}$. The background activity was greatly reduced by the presence of the non-ionic detergent Triton X-100 at a final concentration of 1% (Table 3); in contrast, the specific KEX2 endopeptidase was slightly activated by such treatment (Table 3) and readily solubilized from membranes by this detergent (Table 4). The specific endopeptidase appeared to be more susceptible to inhibition by the sulfhydryl group reagents iodoacetic acid, and iodoacetamide than the background activity; conversely, the specific endopeptidase was much less sensitive to inactivation by organic solvents, including dimethyl sulfoxide, methanol and formamide, than the background activity. Finally, the specific endopeptidase appeared to have a pH optimum of 7.0–7.5, with little activity detected at pH 5.0 and about half-maximal activity at pH 8.5.

TABLE 1

Yeast strains used.

| Strain | Genotype | Source |
|---|---|---|
| XBH16-15A | MATα kex2-1 ade2-1 his⁻ leu2-3,112 trp1-289 ura3-52 [KIL-k] | L. Blair |
| XBH16-13C | MATa kex2-1 his⁻ leu2-3,112 ura3-52 [KIL-k] | L. Blair |
| XBH6-13D | MATα cry1 lys1-1 | L. Blair |
| XBH8-2C | MATα sst2-4 his6 met⁻ ura1 | L. Blair |
| XBH75-2A | MATα kex2-1 sec1-1 ade2 leu2-3,112 ura3-52 | L. Blair |
| XBH76-1A | MATα kex2-1 sec18-1 ade2 leu2-3,112 ura3-52 | L. Blair |
| XBH77-7D | MATα kex2-1 sec7-1 ade2 leu2-3,112 ura3-52 | L. Blair |
| XBH78-10B | MATα kex2-1 sec53-6 leu2-3,112 trp1-289 ura3-52 | L. Blair |
| AB35-13D | MATa leu2-3,112 ura3-52 ade2 his4 trp1 | A. Brake |
| AB35-14A | MATα leu2-3,112 ura3-52 | A. Brake |
| RW78 | MATα kex2-1 his7 | R. Wickner |
| RW427 | MATα kex2-4 ade1 thr1 ura1 | R. Wickner |
| RW433 | MATα kex2-15 leu2 | R. Wickner |
| RW720 | MATa ade2 leu2 [KIL-0] | R. Wickner |
| RW721 | MATα ade2 leu2 [KIL-0] | R. Wickner |
| DC17 | MATα his1 [KIL-0] | J. Hicks |
| DC227 | MATa cry1-3 lys1-1 | J. Hicks |
| RC634 | MATa sst1-3 ade2 his6 met1 ura1 rme1 | R. Chan |
| SF282-6A | MATα sec18-1 | C. Field |

LEGEND FOR TABLE 1
For certain experiments, diploids were prepared by crossing two of the strains listed above. The parental strains of such crosses are given in the text where appropriate.

TABLE 2

Substrate specificity of endopeptidase activity in membranes from transformed kex2 cells.

| Substrate | Strain | Specific Activity (pmoles AMC formed/μg protein 10 min) | Relative Ratio |
|---|---|---|---|
| Boc—GlnArgArg—MCA | kex2[YEp24] | 5.0 | [1.0] |
|  | kex2[YEp24-pJ2B] | 100.8 | 20.2 |
|  | kex2::pJ2B | 16.7 | 3.3 |
| Boc—GluLysLys—MCA | kex2[YEp24] | 0.3 | [1.0] |
|  | kex2[YEp24-pJ2B] | 1.9 | 6.3 |
|  | kex2::pJ2B | 0.5 | 1.7 |
| Arg—MCA | kex2[YEp24] | 6.7 | [1.0] |
|  | kex2[YEp24-pJ2B] | 14.0 | 2.1 |
|  | kex2::pJ2B | 8.0 | 1.2 |
| Leu—MCA | kex2[YEp24] | 33.7 | [1.0] |
|  | kex2[YEp24-pJ2B] | 69.8 | 2.1 |
|  | kex2::pJ2B | 37.9 | 1.1 |
| Bz—Arg—MCA | kex2[YEp24] | 0.1 | [1.0] |
|  | kex2[YEp24-pJ2B] | 0.6 | 6.0 |
|  | kex2::pJ2B | 0.1 | 1.0 |
| Boc—IleGluGlyArg—MCA | kex2[YEp24] | 0.3 | [1.0] |
|  | kex2[YEp24-pJ2B] | 5.8 | 19.3 |
|  | kex2::pJ2B | 0.9 | 3.0 |
| Boc—PheSerArg—MCA | kex2[YEp24] | 0.6 | [1.0] |
|  | kex2[YEp24-pJ2B] | 31.0 | 51.7 |
|  | kex2::pJ2B | 3.8 | 6.3 |

LEGEND FOR TABLE 2
Cells of strain XBH16-15A that had been transformed with the plasmids indicated, or that contained pJ2B in integrated form, were grown in SC-Ura and membranes were prepared as described in the Experimental. Endopeptidase activity was assayed as described in the Experimental. All substrates tested were present at 0.1 mM.

TABLE 3

Susceptibility to various inhibitors of endopeptidase activity in membranes from transformed kex2 cells.

| Strain | Inhibitor | | Specific Activity (pmoles/μg/10 min) | Inhibition (%) | Relative Ratio |
|---|---|---|---|---|---|
| kex2[YEp24] | None | | 5.1 | — | |
| | + PMSF, | 1 mM | 2.8 | 45 | |
| | | 5 mM | 1.5 | 71 | |
| | + TLCK, | 1 mM | 2.3 | 55 | |
| | | 5 mM | 1.8 | 65 | |
| | + TPCK, | 1 mM | 2.2 | 57 | |
| | | 5 mM | 1.4 | 73 | |
| | + Triton X-100, | 1% | 1.5 | 71 | |
| | | 1% + 5 mM TPCK | 1.2 | 76 | [1.0] |
| kex2[YEp24-pJ2B] | None | | 108.5 | — | |
| | + PMSF, | 1 mM | 116.7 | 0 | |
| | | 5 mM | 110.2 | 0 | |
| | + TLCK, | 1 mM | 100.8 | 7 | |
| | | 5 mM | 95.5 | 12 | |
| | + TPCK, | 1 mM | 105.9 | 2 | |
| | | 5 mM | 109.2 | 0 | |
| | + Triton X-100, | 1% | 155.0 | 0 | |
| | | 1% + 5 mM TPCK | 152.9 | 0 | 127.4 |
| kex2::pJ2B | None | | 17.4 | — | |
| | + PMSF, | 1 mM | 14.4 | 17 | |
| | | 5 mM | 14.7 | 16 | |
| | + TLCK, | 1 mM | 14.6 | 16 | |
| | | 5 mM | 14.5 | 17 | |
| | + TPCK, | 1 mM | 14.3 | 18 | |
| | | 5 mM | 15.2 | 13 | |
| | + Triton X-100, | 1% | 12.9 | 26 | |
| | | 1% + 5 mM TPCK | 11.4 | 34 | 9.4 |

LEGEND FOR TABLE 3
Cells of strain XBH16-15A that had been transformed with the plasmids indicated, or that contained pJ2B in integrated form, were grown in SC-Ura and membranes were prepared as described in the Experimental. Endopeptidase activity was assayed using Boc—GlnArgArg—MCA as the substrate, as outlined in the Experimental. All inhibitors were added from a 0.1 M stock dissolved in dimethyl sulfoxide. All values given were corrected for the slight effects of addition of this solvent alone.

TABLE 4

Release of endopeptidase activity from membranes by detergent treatment.

| Condition | Fraction | Specific Activity (pmoles/μg/10 min) | % of Total | % of Recovery |
|---|---|---|---|---|
| −1% Triton X-100 | Whole lysate | 150.0 | [100] | |
| | P100 | 130.0 | 87 | |
| | | | | 104 |
| | S100 | 26.0 | 17 | |
| +1% Triton X-100 | Whole lysate | 265.0 | [100] | |
| | P100 | 50.0 | 19 | |
| | | | | 94 |
| | S100 | 200.0 | 75 | |

Strain XBH16-15A carrying the KEX2 gene on a multi-copy plasmid (YEp24-pJ2B) was grown to mid-exponential phase in SC-Ura. The cells were collected by centrifugation and a lysate was prepared as described in the Experimental. The lysate was divided into two equal portions, one of which was treated with the non-ionic detergent Triton X-100 at a final concentration of 1%. Samples of both the original lysate and the detergent-treated lysate were saved and the remainder of each was separated into a crude membrane fraction (P100) and a soluble fraction (S100) by centrifugation at 100,000 × g for 1 hr for endopeptidase activity using Boc—GlnArgArg—MCA as the substrate, as given in the Experimental.

To further define the region containing the KEX2 gene, plasmid pJ2B was digested either partially or to completion with a variety of restriction enzymes (SalI, EcoRI, BamHI, SacI and BglII) and then religated and the resulting products used to transform E. coli HB101 to ampicillin resistance. The resulting transformants were then screened to identify those carrying plasmids which still contain the 2μm and URA3 segments of YEp24. These plasmids were then used to transform yeast strain XBH16 - 15a and the resultant Ura+ transformants tested to determine which were also KEX2+, as demonstrated by their ability to secrete α-factor, using the α-factor halo assay.

An alternative method involved digestion of pJ2B with BamHI and/or BglII and subcloning into the BamHI site of pAB18. Plasmid pAB18 was constructed by insertion of ClaI-digested 2μm DNA into the ClaI site of YIp5 (Botstein et al., Gene (1979) 8:17). The resulting plasmids were used to transform XBH16-15a and Ura+ transformants tested for complementation of the kex2 mutation as described previously.

Using the above methods, the region of the original insert required for complementation of the kex2 mutation was localized to a segment containing the 3.5kb EcoRI fragment shown in FIG. 3 as KEX1-2, a 3'-end truncated KEX2 gene. A 5kb BamHI-SacI fragment containing the complete gene shown as KEX4-5 is also shown in FIG. 3, the preparation of which is described below. Direction of transcription is indicated by an arrow in FIG. 3. The EcoRI fragment was ligated into the BamHI site of pAB18 after repair of the EcoRI ends with the DNA polymerase I Klenow fragment and addition of BamHI linkers, followed by BamHI digestion. The resulting plasmid pAB222 was found to complement the kex2 mutation by the procedures described above.

Enhanced Processing of Proinsulin Using a KEX2 Containing Plasmid

Plasmids containing both the KEX2 gene (complete or 3'-end truncated) and an α-factor leader-proinsulin gene fusion were constructed (pYBCA5-KEX2 and pYBCA5-KEX4). Two fragments of different sizes containing the truncated KEX2 gene (3.5 Kb) or complete KEX2 gene (about 5 Kb) were cloned into pYBCA5.

I. Construction of pYBCA-5.

A nucleotide sequence designated BCA-5 based on the amino acid sequence for human proinsulin, reported by Bell et al. (Bell, G. I., Swain, W. F., Pictec, R., Cordell, B., Goodman, H. M. and Rutter, W. J., *Nature* (1979) 282:525-527) and employing yeast preferred codons was devised. This sequence, which encodes for peptides, B, C and A of human proinsulin, is shown in FIG. 1.

The sequence includes a KpnI cohesive end at the 5'-end and a SalI cohesive end at the 3'-end of the coding strand. Coding for the mature secreted peptide begins after the LysArg processing site. The 5'-end of the synthetic sequence is a modification of the 3'-end of the naturally-occurring α-factor secretory leader and processing signal sequence, where three glu-ala pairs have been deleted. The 3'-end of the synthetic sequence includes two translational stop codons.

Synthetic DNA fragments having the sequence just described were prepared by synthesizing overlapping ssDNA segments using the phosphoramidite method as described by Beaucage and Carruthers (1981) *Tetrahedron Lett.* 27:1859-1862, and annealing and ligating under the following conditions.

The ssDNA fragments were joined as follows: 50 to 100 pmoles of each segment (except the two segments at the 5'-terminii) were 5'-phosphorylated with 5-6 units of T4 polynucleotide kinase (New England Nuclear) in 10 mM dithiothreitol (DTT), 1 mM ATP, 10 mM MgCl$_2$, 100 ng/ml spermidine, 50 mM Tris-HCl, pH 7.8 (total volume: 20 μl) for 30 min at 37° C. Additional T4 kinase (5.6 units) was then added and the reaction continued for 30 min at 37° C. The fragments (except for the 5' termini) were combined, diluted to 40 ul with water, 60 ul of 1 M sodium acetate, 12 ul of 250 mM EDTA and 5 ug of 1 mg/ml poly-A were added. After heating for 5 min at 65° C., the 5' terminal pieces were added, followed by 420 ul of ethanol (100%). The solution was chilled for 20 min at −80° C., centrifuged and the pellet was washed once with ethanol (100%) and dried. The pellet was redissolved in water (18 μl) and heated to 100° C. for 3 minutes and then cooled slowly over 1.5 hours to 25° C. in a water bath.

The annealed fragment pool was ligated in a reaction mixture containing T4 DNA ligase (Bio Labs, 1200 units) 1 mM ATP, 10 mM DTT, 10 mM MgCl$_2$, 100ng/ml spermidine, and 50 mM Tris-HCl, pH 7.8 (30μl). After 1 hour at 14° C., the reaction mixture was partially purified by preparative polyacrylamide gel (7%, native) electrophoresis. The DNA was removed from the appropriate gel slice by electroelution and ethanol coprecipitation with polydA (5 μg).

After assembly the synthetic BCA-5 fragment was substituted into a KpnI/SalI digested bacterial cloning plasmid pAB114αEGF-24, which plasmid was prepared by mutagenesis of pYEGF-8 and pAB114 (see FIG. 2). The plasmid resulting from the insertion was designated pAB114αBCA5.

The preparation of pAB114 was as follows: Plasmid pAB101 was obtained by screening a yeast genomic library cloned in YEp24 (Fasiolo, et al., 1981, *J. Biol. Chem.*, 256:2324) using a synthetic 20-mer oligonucleotrde probe (5'-TTAGTACATTGGTTGGCCGG-3') homologous to the published α-factor coding region (Kurjan and Herskowitz, Abstracts 1981, Cold Springs Harbor meeting on the Molecular Biology of Yeasts, page 242). Plasmid AB11 was obtained by deleting the HindIII to SalI region of pBR322. An EcoRI fragment of pAB101 carrying the α-factor gene was then inserted into the unique EcoRI site in pAB11 to produce pAB112. Plasmid pAB112 was digested to completion with HindIII, and then religated at low (4 μg/ml) DNA concentration to produce plasmid pAB113 in which three 63bp HindIII fragments were deleted from the α-factor structural gene, leaving only a single copy of mature α-factor coding region. A BamHI site was added to plasmid pAB11 by cleavage with EcoRI, filling in of the overhanging ends by the Klenow fragment of DNA polymerase, ligation of BamHI linkers and religation to obtain a plasmid designated pAB12. Plasmid pAB113 was digested with EcoRI, the overhanging ends filled in, and ligated to BamHI linkers. After digestion with BamHI, the resulting 1500bp fragment was gelpurified and ligated to pAB12 which had been digested with BamHI and treated with alkaline phosphatase to produce pAB114, which contains a 1500 bp BamHI fragment carrying the α-factor gene.

The preparation of pYEGF-8 was as follows: A synthetic sequence for human epidermal growth factor (EGF) was prepared and ligated to pAB112 (described above) which had been previously completely digested with HindIII and SalI to produce pAB201. The HindIII site lies within the 3'-end of the α-factor gene, and the EGF sequence was inserted using appropriate linkers. The resulting plasmid was designated pAB201.

Plasmid pAB201 (5 μg) was digested to completion with EcoRI and the resulting fragments were filled in with DNA polymerase I Klenow fragment and ligated to an excess of BamHI linkers. The resulting 1.75 kbp fragment was isolated by preparative gel electrophoresis, and approximately 100 ng of this fragment was ligated to 10 ng of yeast plasmid pCl/1 (described below) which had been previously digested t completion with restriction enzyme BamHI and treated with alkaline phosphatase. The ligation mixture of the 1.75 kbp fragment carrying the α-factor gene and pCl/1 was used to transform *E. coli* HB101 cells, and transformants were selected based on ampicillin resistance. DNA from one ampicillin resistant clone (designated pYEGF-8) was used to transform yeast AB103 (genotype: MATα. pep 4-3, leu 2-3, leu 2- 112, ura 3-52, his 4-580) cells, and transformants selected based on their leu+ phenotype.

Plasmid pCl/1 is a derivative of pJDB219 (Beggs (1978) Nature 275:104) where the region derived from bacterial plasmid pMB9 has been replaced by pBR322. The pCl/1 plasmid carries genes for both ampicillin resistance and leucine prototrophy.

Plasmid pAB114αEGF-24 was obtained as follows: a PstI-SalI fragment of pYEGF-8 containing the α-factor leader hEGF fusion was cloned in phage M13 and isolated in single-stranded form. A synthetic 36-mer oligonucleotide primer (5'-GGGGTACCTTT-GGATAAAAGAAACTCCGACTCCGAA-3') was used as a primer for the synthesis of the second strand using the Klenow fragment of DNA polymerase I. After fill-in and ligation at 14° C. for 18 hours, the mixture was treated with S$_1$ nuclease and used to transfect *E. coli* JM101 cells. Phage containing DNA sequences in which the glu-ala region was removed were located using $^{32}$P-labelled primer as a probe. DNA from positive plaques was isolated, digested with PstI and SalI, and the resulting fragment inserted into pAB114 (described above) which has been previously digested to completion with SalI, partially with PstI and treated with alkaline phosphatase. The resulting plasmid was designated pAB114αEGF-24.

Referring again to FIG. 2, the BamHI-BamHI fragment of pAB114αBCA-5 was excised and ligated into the unique BamHI site of pCl/1. The resulting expression vector was designated pYBCA-5.

2. Insertion of KEX2 gene into pYBCA-5

The two fragments of different sizes containing a truncated or a complete KEX2 gene were independently cloned into the above plasmid. The first corresponds to the 3.5 kb EcoRI fragment which contains a 3+-end truncated KEX2 gene and the second corresponds to the BamHI-SacI fragment which contains the complete KEX2 gene.

A. Cloning of the truncated KEX2 gene (3.5 Kb EcoRI-fragment)

FIG. 5 shows the partial DNA sequence of the KEX2 gene and predicted amino acid sequence. The arrows indicate EcoRI sites that yield the 3.5 Kb fragment coding for a 3'-end truncated gene. This fragment was purified by gel electrophoresis and was ligated to BamHI linkers after the sticky ends were filled in with Klenow. After digestion with BamHI, the fragment was ligated to BamHI digested and alkaline phosphatase treated pAB18 to produce pAB222. pAB18 was obtained by cloning ClaIdigested 2μm plasmid into YIp5 (Botstein et al., 1979, Gene 1:17) previously digested with ClaI and treated with alkaline phosphatase. pAB222 was digested with BamHI and the resulting 3.5 Kb (EcoRI)BamHI-(EcoRI)BamHI fragment was purified by gel electrophoresis and ligated to BglII digested, alkaline phosphatase treated pYBCA-5. The BglII site is approximately 940 bp upstream of the α-factor structural gene. The plasmid pYBCA5-KEX2 was obtained in which the direction of transcription of the KEX2 gene is opposite that of the proinsulin gene (FIG. 4).

B. Cloning of the complete KEX2 gene (5 kb BamHISacI fragment)

This longer fragment (KEX 4-5) which corresponds to a BamHI-EcoRI fragment fused to a EcoRI-SacI fragment (FIG. 3) was obtained by a series of deletions of the original genomic insert shown in FIG. 3. (Please note: The EcoRI-SacI fragment is not involved with the KEX2 structural gene, but for simplicity of construction procedures it was included in the subject construction.) Plasmid pJ2B, which contains the 13.5 kb genomic insert was partially digested with EcoRI and self-ligated to produce pAB217 which contains a 6 Kb deletion upstream of the KEX2 gene in the 5' non-coding region. pAB217 was partially digested with BamHI and self-ligated to produce pAB218 which contains a 2 Kb deletion downstream the KEX2 gene in the 3' non-coding region. pAB218 was digested with SacI, the protruding ends were blunted with Klenow in the absence of deoxynucleosides and ligated to BamHI linkers. Following BamHI digestion, an about 5 Kb BamHI-(SacI)BamHI fragment was purified by gel electrophoresis. This fragment was ligated to BglII digested, phosphatase alkaline treated pYBCA-5 to produce pYBCA5-KEX4 (FIG. 4).

3. Processing of Proinsulin Using KEX2 Containing Vectors

Plasmids containing proinsulin and KEX2 genes (pYBCA5-KEX2 or pYBCA5-KEX4) or control plasmids with only proinsulin sequences (pYBCA5) or no insert (pCl/1) were used to transform kex2$^-$ mutant yeast strain AB109 (Matα, kex2-1, ade2-1, his$^-$, leu2-3,112, trpl$^{-289}$, ura3-25 ura3-52, (KIL-k), cir° ) or KEX2$^+$ yeast strain AB103.1 (matα, pep4-3, leu2-3, leu2-112, ura3-52, his4-580, cir° ) following the procedure of Hinnen et al., *Proc. Natl. Acad. Sci. USA* (1978) 75:1929-1933. Transformants were grown in a low sulfate medium (LSM) containing 0.1 mM (NH$_4$)$_2$SO$_4$ until mid-exponential phase (OD$_{660\ nm}$ 1-3), collected by centrifugation and resuspended in LSM containing 0.25 mCi of carrier free [$^{35}$S]SO$_4^{2-}$ at an OD$_{660}$=2. After 10 min incubation, a 50-fold excess of (NH$_4$)$_2$SO$_4$ was added and cells were further incubated for 15-30 min. After centrifugation, proteins present in the cell free extract were precipitated with 12% trichloroacetic acid, 0.5 mg/ml deoxycholate. The precipitate was resuspended, reduced and alkylated and submitted to protein acrylamide gel electrophoresis (Laemmli, *Nature* (1970) 227:680). Gels were fixed, fluorographed, dried and exposed to Kodak XAR-5 film at −70° C.

Autoradiographic results show that mainly high molecular weight insulin related bands (23.5 Kd and > 43 Kd) are present in cell free extracts of KEX2$^-$ mutant strains (AB109) transformed with pYBCA5. The >43 Kd band corresponds to an overglycosylated proinsulin-leader precursor and the 23.5 Kd to a proinsulin-leader peptide. When the same kex2$^-$ mutant strain is transformed with pYBCA5-KEX2, insulin-related products of smaller molecular weights are obtained. A band of approximately 10 Kd corresponding to proinsulin is detected, as well as smaller bands of 7-7.5 Kd corresponding to B/C fusion and 3 kd corresponding to A or B chains. Similar results are obtained with the KEX2$^+$ strain AB103.1. When this strain is transformed with pYBCA5, several insulin-related bands (>43 Kd, 23.5 Kd, 10 Kd, 7.5 Kd, 3 Kd) corresponding to the different species described above, are obtained. The high molecular weight bands are particularly predominant (>43 Kd and 23.5 Kd). When these species are submitted to oxidative sulfitolysis (Cole, *Methods in Enzymology* (1967) 11:206) and separated by acrylamide gel electrophoresis, a large amount of A chain is detected, while there is very little B chain. When this same strain is transformed with pYBCA5-KEX2, the banding pattern of insulin related material and the relative amounts of A and B chain changes. High molecular weight bands (>43 Kd and 23.5 Kd) practically disappear, while low molecular weight bands (3 Kd) increase considerably, as determined by densitometric scanning of the autoradiogram. Analysis of A and B chain by oxidative sulfitolysis (Cole, supra) shows an increased amount of B chain. These results clearly show that the KEX2 endopeptidase synthesized from the gene present in the plasmid, is able to process proinsulin at specific cleavage sites (between α-factor leader and proinsulin, at the B/C chain junction and at the C/A chain junction).

Following the procedure described above, another construction was made where the sequence was modified by changing two nucleotides of the codon coding for amino residue 31 (arg) of the proinsulin to replace this residue by lysine. This replacement was made to have lys-arg as the dibasic sequence which is cleaved at all junctions within the proinsulin gene (boxes in FIG. 1), since this is the sequence found at the cleavage site of the α-factor precursor.

It is evident from the above results that large amounts of the endopeptidase expression product of the KEX2 gene can be obtained for purification and use in vitro for the processing of polypeptides at specific cleavage sites. Furthermore, yeast or analogous hosts may be developed which allow for enhanced processing of expression products of polypeptides of interest, such as pathogenic polypeptides or mammalian polypeptides, which may find use for in vitro or in vivo purposes. Therefore, vectors and hosts can be provided which will provide for more economic and efficient production of a wide variety of polypeptides of interest.

Although the foregoing invention has been described in some detail by way of illustration and example for purposes of clarity of understanding, it will be obvious that certain changes and modifications may be practiced within the scope of the appended claims.

What is claimed is:

1. A composition consisting essentially of DNA molecules comprising a structural gene encoding a KEX2 polypeptide lacking 0–60 amino acids from the C-terminus, wherein the polypeptide has KEX2 endopeptidese activity, and wherein said DNA molecules are about 10 kbp or less in length and are substantially free of DNA molecules not encoding a KEX2 polypeptide.

2. A replication vector comprised of a structural gene encoding a KEX2 polypeptide lacking 0–60 amino acids from the C-terminus, wherein the polypeptide has KEX2 endopeptidase activity.

3. A composition comprising a host cell, wherein the host cell is transformed with DNA encoding a KEX2 polypeptide lacking 0–60 amino acids from the C-terminus, wherein the polypeptide has KEX2 endopeptidase activity, and further wherein the composition is substantially free of host cells not transformed with the DNA.

4. The host cell of claim 3, wherein the genus of the host is a yeast selected from the group consisting of Saccharomyces, Schizosaccharomyces, and Kluveromyces.

5. The host cell of claim 3, further comprising DNA sequences operably linked to the DNA encoding the KEX2 polypeptide and capable of directing expression of said polypeptide in the host cell.

6. The yeast host cell of claim 4, wherein said yeast host cell further comprises a DNA sequence expressible in said yeast host and encoding a precursor polypeptide, wherein the precursor polypeptide is comprised of a processing site recognized by a KEX2 endopeptidase.

7. The yeast host cell of claim 6, wherein the precursor polypeptide is a heterologous polypeptide.

8. The yeast host cell of claim 4, wherein the DNA is further comprised of a heterologous promoter which controls transcription of the KEX2 polypeptide.

9. A method of producing a cleaved polypeptide from a precursor polypeptide comprising:
   (a) providing a KEX2 polypeptide produced by the yeast host cell of claim 4,
   (b) providing a precursor polypeptide which is comprised of a processing site recognized by a KEX2 endopeptidase;
   (c) incubating the precursor polypeptide with the KEX2 polypeptide under conditions which allow cleavage of the precursor polypeptide by the KEX polypeptide; and
   (d) isolating a cleaved polypeptide.

10. A method of producing a cleaved polypeptide from a precursor polypeptide comprising:
    (a) providing a KEX2 polypeptide produced by the host cell of claim 5;
    (b) providing a precursor polypeptide which is comprised of a processing site recognized by a KEX2 endopeptidase;
    (c) incubating the precursor polypeptide with the KEX2 polypeptide under conditions which allow cleavage of the precursor polypeptide by the KEX polypeptide; and
    (d) isolating a cleaved polypeptide.

11. A method of producing a cleaved polypeptide from a precursor polypeptide comprising:
    (a) providing a yeast host cell according to claim 6;
    (b) incubating the yeast host cell under conditions which allow expression of the KEX2 polypeptide and of the precursor polypeptide;
    (c) incubating the KEX2 polypeptide and the precursor polypeptide under conditions which allow cleavage of the precursor polypeptide by the KEX2 polypeptide; and
    (d) isolating a cleaved polypeptide.

12. A method of producing a cleaved polypeptide from a precursor polypeptide comprising:
    (a) providing a yeast host cell according to claim 6;
    (b) incubating the yeast host cell under conditions which allow expression of the KEX2 polypeptide and of the precursor polypeptide and which allow cleavage of the precursor polypeptide by the KEX2 polypeptide; and
    (c) isolating a cleaved polypeptide.

13. A host cell according to claim 3 wherein said host further comprises a DNA sequence expressible in said host and encoding a precursor polypeptide, wherein the precursor polypeptide is comprised of a processing site recognized by a KEX2 endopeptidase.

* * * * *